United States Patent
Sakai et al.

(10) Patent No.: US 10,225,446 B2
(45) Date of Patent: Mar. 5, 2019

(54) IMAGE PICKUP SYSTEM AND LIGHT SOURCE APPARATUS

(71) Applicant: OLYMPUS CORPORATION, Tokyo (JP)

(72) Inventors: Aiko Sakai, Kodaira (JP); Yusuke Yabe, Chofu (JP); Tomoya Takahashi, Hachioji (JP); Satoshi Tanaka, Hachioji (JP); Kotaro Ogasawara, Nakano (JP); Susumu Hashimoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 125 days.

(21) Appl. No.: 15/368,580

(22) Filed: Dec. 3, 2016

(65) Prior Publication Data

US 2017/0085763 A1 Mar. 23, 2017

Related U.S. Application Data

(63) Continuation of application No. PCT/JP2015/078020, filed on Oct. 2, 2015.

(30) Foreign Application Priority Data

Oct. 10, 2014 (JP) .................................. 2014-209227

(51) Int. Cl.
*H04N 5/225* (2006.01)
*A61B 1/00* (2006.01)
(Continued)

(52) U.S. Cl.
CPC ....... *H04N 5/2256* (2013.01); *A61B 1/00163* (2013.01); *A61B 1/06* (2013.01);
(Continued)

(58) Field of Classification Search
CPC combination set(s) only.
See application file for complete search history.

(56) References Cited

U.S. PATENT DOCUMENTS

| 2014/0049624 A1* | 2/2014 | Masaki | .............. A61B 1/00006 348/68 |
|---|---|---|---|
| 2014/0171738 A1* | 6/2014 | Kagaya | .................. A61B 1/051 600/109 |

FOREIGN PATENT DOCUMENTS

| JP | 2009-201767 A | 9/2009 |
|---|---|---|
| JP | 2013-90884 A | 5/2013 |

(Continued)

OTHER PUBLICATIONS

International Search Report dated Dec. 28, 2015 received in PCT/JP2015/078020.

*Primary Examiner* — Anand S Rao
*Assistant Examiner* — Samuel D Fereja
(74) *Attorney, Agent, or Firm* — Scully, Scott, Murphy & Presser, P.C.

(57) ABSTRACT

An image pickup system includes an optical sensor configured to pick up an optical image of an object illuminated with light of a plurality of colors emitted from a plurality of semiconductor light emitting elements with an image pickup device and detect each of light amounts of the light emitted from the plurality of semiconductor light emitting elements, and a controller including hardware. The controller adjusts color balance based on the light amounts of the plurality of colors detected at the optical sensor and sets an exposure timing of a light amount detecting unit according to image pickup operation of the image pickup device.

11 Claims, 4 Drawing Sheets

(51) Int. Cl.
*A61B 1/06* (2006.01)
*G02B 23/26* (2006.01)
*G02B 23/24* (2006.01)

(52) U.S. Cl.
CPC ..... *G02B 23/2461* (2013.01); *G02B 23/2484* (2013.01); *G02B 23/26* (2013.01); *H04N 2005/2255* (2013.01)

(56) References Cited

FOREIGN PATENT DOCUMENTS

JP          2013-215435 A      10/2013
JP          WO 2013146014 A1 *  10/2013   ......... A61B 1/00006

\* cited by examiner

IMAGE PICKUP SYSTEM AND LIGHT SOURCE APPARATUS

CROSS REFERENCE TO RELATED APPLICATION

This application is a continuation application of PCT/JP2015/078020 filed on Oct. 2, 2015 and claims benefit of Japanese Application No. 2014-209227 filed in Japan on Oct. 10, 2014, the entire contents of which are incorporated herein by this reference.

BACKGROUND OF INVENTION

1. Field of the Invention

The present invention relates to an image pickup system and a light source apparatus, and more particularly, to an image pickup system and a light source apparatus that are using a light emitting element as a light source.

2. Description of the Related Art

As an image pickup system for picking up an image of an object inside a subject to acquire an image, for example, a system which is configured to include an endoscope and a light source apparatus has been conventionally known.

Here, as the endoscope included in the above-mentioned image pickup system, an endoscope which uses, for example, a CCD image sensor (hereinafter, also simply referred to as a "CCD") as an image pickup device for picking up an image of an object is typically known, and an endoscope which uses a CMOS image sensor (hereinafter, also simply referred to as a "CMOS") has been recently proposed.

Further, as the light source apparatus included in the above-mentioned image pickup system, a light source apparatus which uses, for example, a xenon lamp as a light source which supplies illumination light for illuminating an object is typically known, and a light source apparatus which uses a light emitting element such as an LD (laser diode) and an LED (light emitting diode) has been recently proposed.

On the other hand, for example, Japanese Patent Application Laid-Open Publication No. 2013-215435 discloses a light source apparatus for endoscope which uses a blue LD, a red LED, a blue LED and a purple LED as light sources and which has a configuration in which an optical sensor for color balance correction is provided in the vicinity of the blue LD (and each LED).

SUMMARY OF THE INVENTION

An image pickup system according to one aspect of the present invention includes an optical sensor configured to pick up an optical image of an object illuminated with light of a plurality of colors emitted from a plurality of semiconductor light emitting elements with an image pickup device and detect each of light amounts of the light of the plurality of colors emitted from the plurality of semiconductor light emitting elements, and a controller including hardware, and the controller is configured to adjust color balance of the light of the plurality of colors based on the light amounts of the plurality of colors detected at the optical sensor and set an exposure timing of the optical sensor according to image pickup operation of the image pickup device.

A light source apparatus according to one aspect of the present invention includes a plurality of semiconductor light emitting elements configured to emit light of a plurality of colors including light of a predetermined color for illuminating an object, an optical sensor configured to detect each of light amounts of the light of the plurality of colors emitted from the plurality of semiconductor light emitting elements, and a controller including hardware, and the controller is configured to adjust color balance of the light of the plurality of colors based on the light amounts of the plurality of colors detected at the optical sensor and adjust an exposure timing of the optical sensor according to image pickup operation of an image pickup device configured to perform image pickup operation of picking up an optical image of the object illuminated with the light of the plurality of colors, the color balance of which is adjusted.

DETAILED DESCRIPTION OF THE PREFERRED EMBODIMENT(S)

The embodiment of the present invention will be described below with reference to the drawings.

Figure 1:
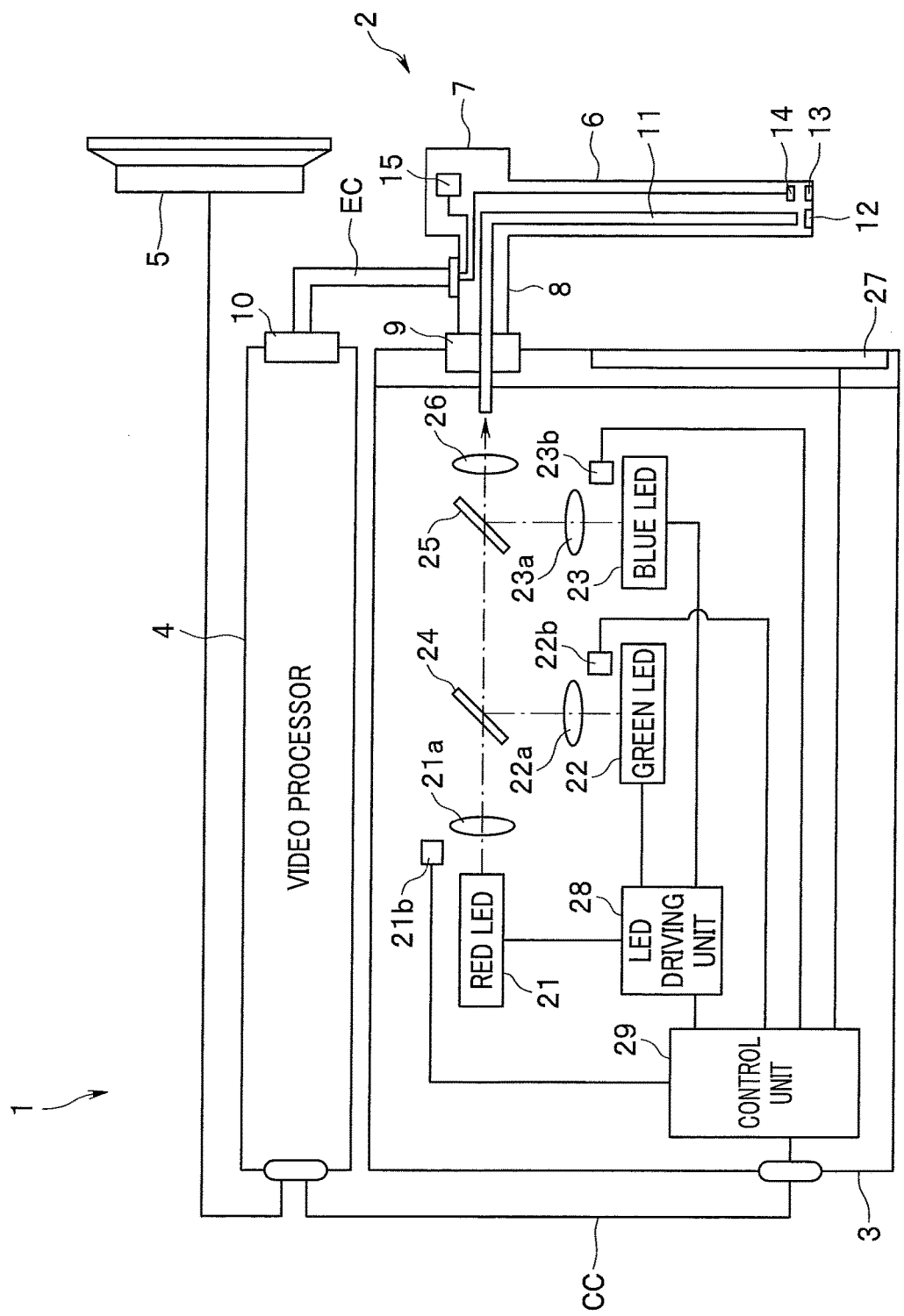
FIG. 1 is a diagram illustrating a configuration of a main part of an image pickup system according to an embodiment.

FIG. 1 to FIG. 4 relate to the embodiment of the present invention. FIG. 1 is a diagram illustrating a configuration of a main part of an image pickup system according to the embodiment.

As illustrated in FIG. 1, the image pickup system 1 includes an endoscope 2 configured to pick up an image of an object inside a subject such as a living body to output an image pickup signal, a light source apparatus 3 configured to supply illumination light for illuminating the object to the endoscope 2, a video processor 4 configured to generate and output an image based on the image pickup signal outputted from the endoscope 2, and a monitor 5 configured to display the image outputted from the video processor 4. Further, the light source apparatus 3 and the video processor 4 are connected via a communication cable CC.

The endoscope 2 is configured to include an elongated insertion portion 6 which can be inserted into the subject, an operation portion 7 formed at a proximal end portion of the insertion portion 6, a universal cable 8 provided to extend from the operation portion 7, an optical connector 9 provided at an end portion of the universal cable 8, and an electrical connector 10 provided at an end portion of an electrical cable EC diverged from the universal cable 8.

The operation portion 7 is configured to have a shape such that a user such as an operator can grip and operate the operation portion 7. Further, at the operation portion 7, one or more scope switches (not illustrated) which can instruct the video processor 4 according to the operation of the user are provided.

The optical connector 9 is configured to be detachably connected to a connector receptacle (not illustrated) of the light source apparatus 3.

The electrical connector 10 is configured to be detachably connected to a connector receptacle (not illustrated) of the video processor 4.

Further, the endoscope 2 is configured to include a light guide 11 configured to transmit illumination light supplied from the light source apparatus 3 to which the optical connector 9 is connected, an illumination lens 12 disposed on an optical path of the illumination light emitted from the light guide 11, an objective lens 13 configured to form an optical image of the object illuminated with the illumination light emitted through the illumination lens 12, an image pickup device 14 configured to perform image pickup operation (exposure and readout) for picking up the optical image formed by the objective lens 13, and a memory 15 in which image pickup device information indicating a type of the image pickup device 14 (for example, either a CCD or a CMOS) and light amount control parameter information indicating a light amount control parameter (which will be described later) set according to the type of the image pickup device 14 are stored in advance.

The light guide 11 is inserted into the insertion portion 6, the operation portion 7 and the universal cable 8. Further, an incident end portion including a light incident surface of the light guide 11 is provided to extend from the optical connector 9. Further, a light emission end portion including a light emission surface of the light guide 11 is disposed in the vicinity of a light incident surface of the illumination lens 12.

The image pickup device 14 has, for example, an electronic shutter function, and is configured using a CCD or a CMOS. Further, the image pickup device 14 is configured to include a plurality of pixels (not illustrated) for performing photoelectric conversion on an optical image formed by the objective lens 13, and a primary color filter (not illustrated) in a Bayer array provided on an image pickup surface on which the plurality of pixels are arranged in two dimensions. Further, the image pickup device 14 generates an image pickup signal by performing photoelectric conversion on the optical image formed by the objective lens 13 and outputs the generated image pickup signal to the video processor 4 to which the electrical connector 10 is connected.

The video processor 4 is, for example, configured to calculate a ratio between average luminance of an image generated based on the image pickup signal outputted from the endoscope 2 and predetermined target luminance and output brightness control information indicating the calculated ratio to the light source apparatus 3.

The video processor 4 is configured to read the image pickup device information and the light amount control parameter information stored in the memory 15 when the electrical connector 10 is connected, and output the read light amount control parameter information to the light source apparatus 3.

The video processor 4 is configured to perform control for operating the image pickup device 14 using a global shutter method when, for example, it is detected that the type of the image pickup device 14 is a CCD based on the image pickup device information read from the memory 15, and output timing information indicating an all pixel exposure period which is a period during which all pixels of the image pickup device 14 are exposed at the same time to the light source apparatus 3. Further, the video processor 4 is configured to perform control for operating the image pickup device 14 using a rolling shutter method when, for example, it is detected that the type of the image pickup device 14 is a CMOS based on the image pickup device information read from the memory 15, and output timing information which allows distinguishing between an all line exposure period which is a period during which pixels located on all horizontal lines of the image pickup device 14 are exposed at the same time, and a non-all line exposure period which is a period other than the all line exposure period, to the light source apparatus 3. That is, the non-all line exposure period is a period except a period during which the pixels located on all the horizontal lines of the image pickup device 14 are exposed at the same time, among the period during which pixels located on at least one horizontal line of the image pickup device 14 are exposed.

The light source apparatus 3 is configured to be able to supply, for example, white light including R light, G light and B light which will be described later as the illumination light for illuminating the object.

The light source apparatus 3 includes a red LED 21 configured to generate R light which is light of a red wavelength band, a lens 21a configured to collect and emit R light, and an optical sensor 21b disposed in the vicinity of the red LED 21 and configured to detect a light amount of the R light emitted from the red LED 21 during an exposure period set by a control unit 29 which will be described later and generate and output a light amount detection signal indicating the detected light amount.

The optical sensor 21b has, for example, an electronic shutter function, and is configured to be able to change an exposure period during which the light amount of the R light emitted from the red LED 21 is detected according to setting of the control unit 29.

The light source apparatus 3 includes a green LED 22 configured to generate G light which is light of a green wavelength band, a lens 22a configured to collect and emit G light, and an optical sensor 22b disposed in the vicinity of the green LED 22 and configured to detect a light amount of G light emitted from the green LED 22 during an exposure period set by the control unit 29 which will be described later and generate and output a light amount detection signal indicating the detected light amount.

The optical sensor 22b has, for example, an electronic shutter function, and is configured to be able to change an exposure period during which the light amount of the G light emitted from the green LED 22 is detected according to setting of the control unit 29.

The light source apparatus 3 includes a blue LED 23 configured to generate B light which is light of a blue wavelength band, a lens 23a configured to collect and emit B light, and an optical sensor 23b disposed in the vicinity of the blue LED 23 and configured to detect a light amount of the B light emitted from the blue LED 23 during an exposure period set by the control unit 29 which will be described later, and generate and output a light amount detection signal indicating the detected light amount.

The optical sensor 23b has, for example, an electronic shutter function, and is configured to be able to change an exposure period during which the light amount of the B light emitted from the blue LED 23 is detected according to setting of the control unit 29.

The light source apparatus 3 includes a dichroic mirror 24 configured to have optical characteristics such that the R light emitted through the lens 21a is transmitted to the connector receptacle side and the G light emitted through the lens 22a is reflected to the connector receptacle side.

The light source apparatus 3 includes a dichroic mirror 25 configured to have optical characteristics such that the R light and G light emitted through the dichroic mirror 24 are transmitted to the connector receptacle side and the B light emitted through the lens 23a is reflected to the connector receptacle side.

The light source apparatus 3 includes a lens 26 configured to collect the R light, the G light and the B light emitted through the dichroic mirror 25 and emit the light to a light incident surface of the light guide 11 disposed in the vicinity of the connector receptacle in accordance with connection of the optical connector 9.

The light source apparatus 3 includes, for example, an operation panel 27 including a user interface which allows operation relating to switching between ON/OFF of a power supply, operation relating to setting of color balance, or the like.

The light source apparatus 3 includes an LED driving unit 28 configured to generate and output an LED drive signal for driving the red LED 21, the green LED 22 and the blue LED 23 according to control of the control unit 29 which will be described later.

The light source apparatus 3 includes a control unit 29 configured to control the LED driving unit 28 to adjust the light amounts of the R light, the G light and the B light based on the light amount detection signals respectively outputted from the optical sensors 21b, 22b and 23b, the brightness control information, the light amount control parameter information and the timing information outputted from the video processor 4.

The control unit 29 is configured to set a light amount control pattern GP for adjusting the light amount of the G light emitted from the green LED 22 which is a reference LED based on the light amount control parameter information and the timing information outputted from the video processor 4. Further, the control unit 29 is configured to set the exposure period of the optical sensor 22b based on the timing information outputted from the video processor 4 and the light amount control pattern GP. Still further, the control unit 29 is configured to control the LED driving unit 28 to drive the green LED 22 so that the G light of the light amount according to the brightness control information is emitted for each one field period based on the brightness control information outputted from the video processor 4, and the light amount control pattern GP.

The control unit 29 is configured to adjust the light amount of the R light emitted from the red LED 21 which is different from the reference LED using a control pattern which is the same as the light amount control pattern GP applied to the green LED 22. Further, the control unit 29 is configured to set an exposure period of the optical sensor 21b so as to be the same exposure period as that of the optical sensor 22b. Still further, the control unit 29 is configured to calculate a light amount ratio so that predetermined color balance or color balance set according to operation of the operation panel 27 can be achieved as a light amount ratio of the R light in the case where the light amount of the G light is used as a reference light amount based on the light amount detection signal outputted during the exposure period of the optical sensor 21b, the light amount detection signal outputted during the exposure period of the optical sensor 22b and the light amount control pattern GP, and control the LED driving unit 28 to drive the red LED 21 with the light amount according to the calculated light amount ratio for each one field period.

The control unit 29 is configured to adjust the light amount of the B light emitted from the blue LED 23 which is different from the reference LED using a control pattern which is the same as the light amount control pattern GP applied to the green LED 22. Further, the control unit 29 is configured to set an exposure period of the optical sensor 23b so as to be the same exposure period as that of the optical sensor 22b. Still further, the control unit 29 is configured to calculate a light amount ratio so that predetermined color balance or color balance set according to operation of the operation panel 27 can be achieved as a light amount ratio of the B light in the case where the light amount of the G light is used as a reference light amount based on the light amount detection signal outputted during the exposure period of the optical sensor 23b, the light amount detection signal outputted during the exposure period of the optical sensor 22b and the light amount control pattern GP and control the LED driving unit 28 to drive the blue LED 23 with a light amount according to the calculated light amount ratio for each one field period.

That is, the control unit 29 has a function as a color balance adjusting unit and is configured to adjust color balance of the R light, the G light and the B light by performing control for driving the red LED 21 and the blue LED 23 based on the light amount detection signals outputted during the exposure periods of the optical sensors 21b to 23b and the light amount control pattern GP.

Operation, or the like, of the image pickup system 1 of the present embodiment will be described next. Note that, in the following description, setting of the exposure period of the optical sensor 22b which is a reference LED will be specifically described. Further, in the following description, assuming that the same exposure period as that of the optical sensor 22b is set as the exposure periods of the optical sensors 21b and 23b, specific description relating to setting of the exposure periods of the optical sensors 21b and 23b will be omitted. Still further, in the following description, a case where the object is illuminated with white light including the R light, G light and B light will be described.

Figure 2:
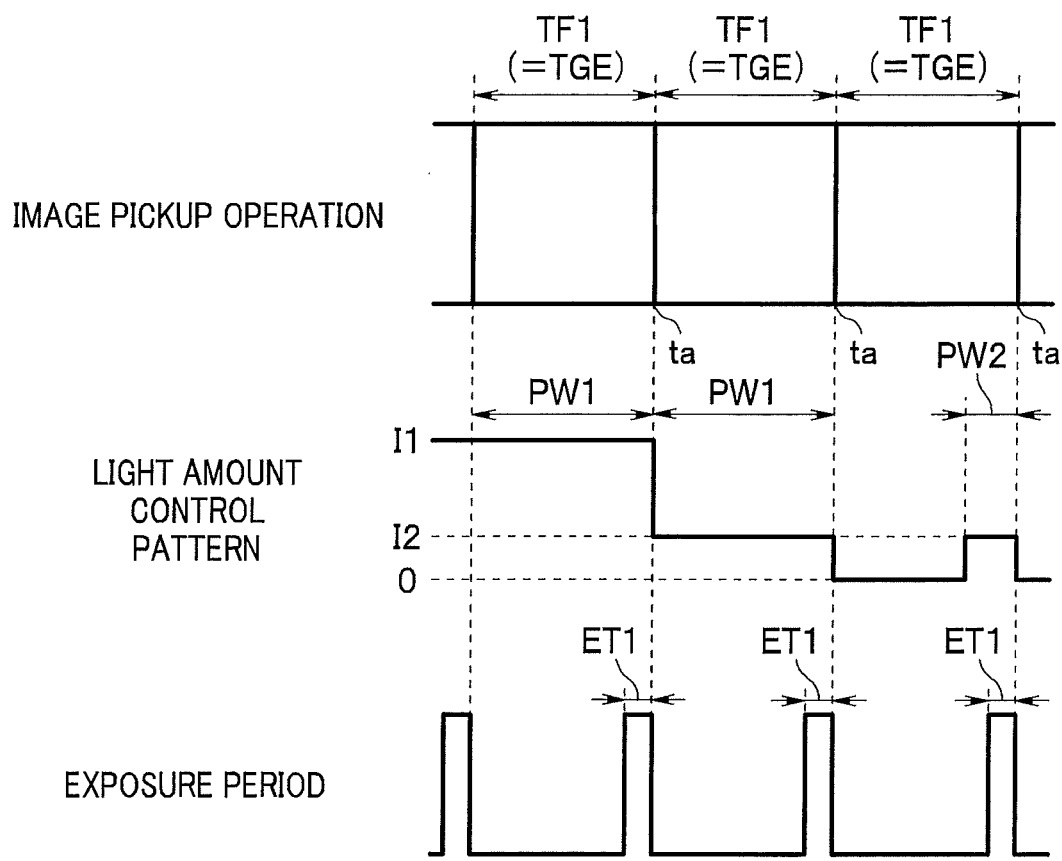
FIG. 2 is a timing chart for explaining an example of operation of the image pickup system according to the embodiment.

First, a specific setting method of the exposure period of the optical sensor 22b in the case where the type of the image pickup device 14 is a CCD will be described. FIG. 2 is a timing chart for explaining an example of operation of the image pickup system according to the embodiment.

When it is detected that, for example, the type of the image pickup device 14 is a CCD based on the image pickup device information read from the memory 15 in accordance with connection of the electrical connector 10, the video processor 4 performs control for operating the image pickup device 14 using a global shutter method, and outputs timing information indicating an all pixel exposure period which is a period during which all pixels of the image pickup device 14 are exposed at the same time to the light source apparatus 3. Then, in accordance with such operation of the video processor 4, for example, as illustrated in FIG. 2, image pickup operation which exposes all the pixels of the image pickup device 14 at the same time is performed during one field period TF1, and timing information TJ1 indicating an all pixel exposure period TGE which is the same period as the one field period TF1 is outputted to the light source apparatus 3.

Further, the video processor 4 outputs the light amount control parameter information PJ1 read from the memory 15 in accordance with connection of the electrical connector 10 to the light source apparatus 3.

The control unit 29 sets a light amount control parameter GP1 for adjusting the light amount of the G light by changing a current value of a drive signal for driving the green LED 22 between a maximum current value I1 and a minimum current value I2 based on the light amount control parameter information PJ1 and the timing information TJ1 outputted from the video processor 4 and further changing a pulse width of the drive signal between a maximum pulse width PW1 during the all pixel exposure period TGE (one field period TF1) and a minimum pulse width PW2 during the all pixel exposure period TGE (one field period TF1).

That is, when the type of the image pickup device 14 is a CCD, the light amount control parameter information PJ1 including information indicating the maximum current value I1 and the minimum current value I2 and information indicating the maximum pulse width PW1 and the minimum pulse width PW2 are stored in the memory 15 in advance. Further, when the type of the image pickup device 14 is a CCD, the maximum pulse width PW1 corresponds to a maximum light emitting period in the all pixel exposure period TGE, and the minimum pulse width PW2 corresponds to a minimum light emitting period in the all pixel exposure period TGE.

Note that, it is assumed that, for example, the maximum pulse width PW1 is set as a pulse width matching the all pixel exposure period TGE (one field period TF1).

Here, as illustrated in FIG. 2, the light amount control pattern GP1 is, for example, set as a control pattern such that, when the light amount of the G light is reduced, in the drive signal supplied from the LED driving unit 28 to the green LED 22, control for reducing the current value from I1 to I2 and control for reducing the pulse width from PW1 to PW2 are performed in this order for each one field period TF1. Further, the light amount control pattern GP1 is, for example, set as a control pattern such that, when the light amount of the G light is increased, in the drive signal supplied from the LED driving unit 28 to the green LED 22, control for increasing the pulse width of the drive signal including the current value I2 from PW2 to PW1 and control for increasing the current value of the drive signal from I2 to I1 are performed in this order for each one field period TF1. Note that, in the light amount control pattern GP1, when the pulse width is reduced from PW1 to PW2, control is performed so that a quenching period of the green LED 22 is set in the order closer to a start timing of the all pixel exposure period TGE (one field period TF1).

That is, when the image pickup device 14 performs image pickup operation using a global shutter method, the control unit 29 sets the light amount control pattern GP1 so as to change at least one of a light emitting period (corresponding to the pulse width) and emission intensity (corresponding to the current value) in the all pixel exposure period TGE.

On the other hand, the control unit 29 which has a function as an exposure period setting unit sets an exposure period ET1 of the optical sensor 22b so as to include an end timing to of the all pixel exposure period TGE (one field period TF1) and to be less than the minimum pulse width PW2 based on the timing information TJ1 outputted from the video processor 4 and the light amount control pattern GP1 (see FIG. 2).

Note that, according to the present embodiment, for example, the exposure period ET1 of the optical sensor 22b may be set so as to include a start timing of the all pixel exposure period TGE (one field period TF1) and to be less than the minimum pulse width PW2.

That is, according to operation, or the like, as described above, the exposure period ET1 is set so as to be able to favorably detect the light amount of the G light during a lighting period of the green LED 22 according to the light amount control pattern GP1.

By the way, according to the conventional configuration, for example, when the LED is made to be continuously lighted with the maximum pulse width PW1, in order to secure color balance for a light adjustment range required for the endoscope, it is necessary to detect a light amount of light emitted from the LED using an expensive optical sensor which has a large detection range or a plurality of optical sensors having different detection ranges, that is, a problem arises that manufacturing cost of a system or a light source apparatus becomes high.

On the other hand, according to the present embodiment, for example, because the exposure period ET1 of the optical sensor 22b is set so as to be less than the minimum pulse width PW2, it is possible to favorably detect a light amount of light emitted from the green LED 22 without using an expensive optical sensor having a large detection range or a plurality of optical sensors having different detection ranges, that is, it is possible to reduce manufacturing cost of a system or a light source apparatus compared to the conventional configuration.

Figure 3:
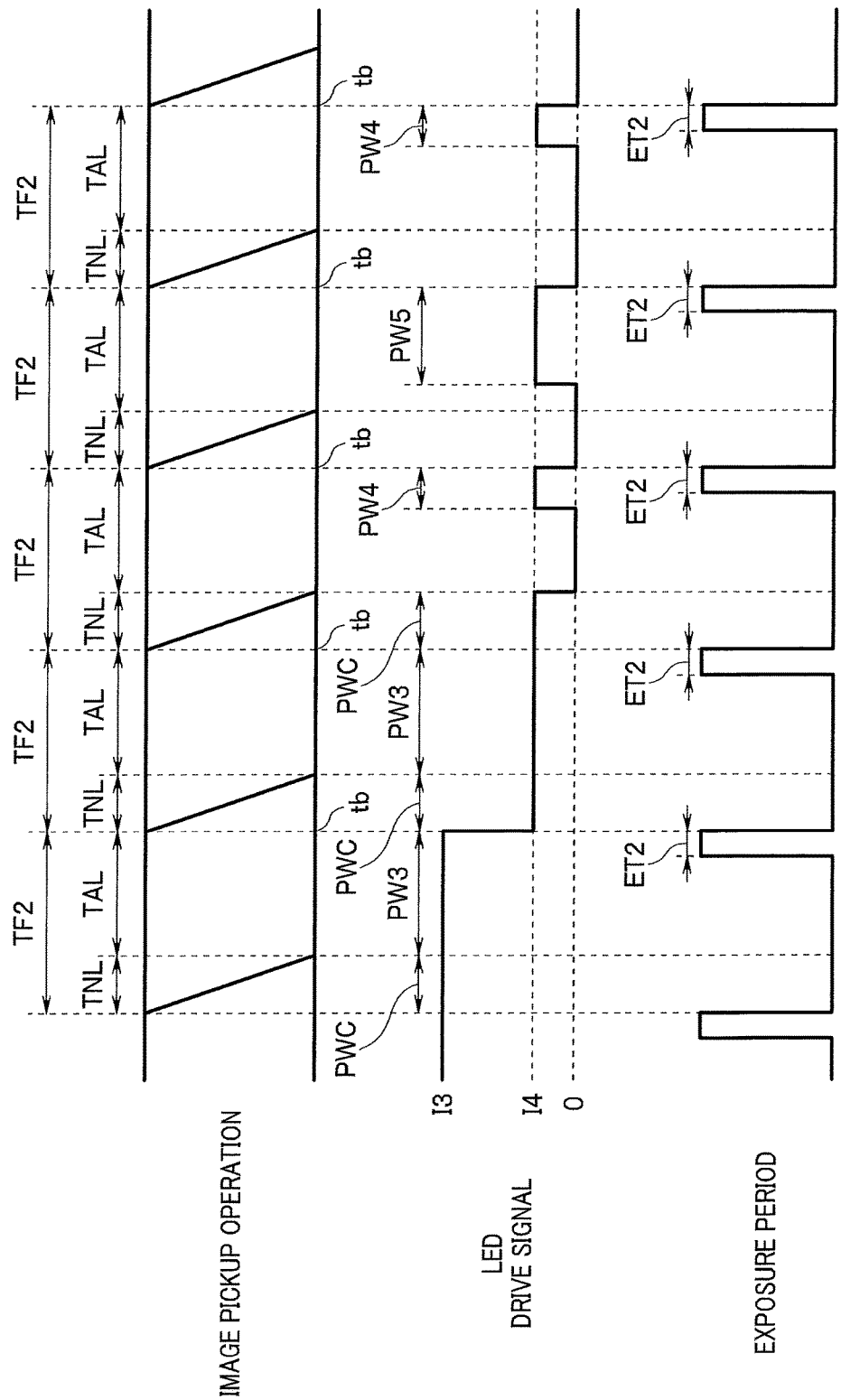
FIG. 3 is a timing chart for explaining an example, which is different from the example in FIG. 2, of the operation of the image pickup system according to the embodiment.

Subsequently, a specific setting method of the exposure period of the optical sensor 22b in the case where the type of the image pickup device 14 is a CMOS will be described. FIG. 3 is a timing chart for explaining an example different from the example in FIG. 2, of operation of the image pickup system according to the embodiment.

When, for example, it is detected that the type of the image pickup device 14 is a CMOS based on the image pickup device information read from the memory 15 in accordance with connection of the electrical connector 10, the video processor 4 performs control for operating the image pickup device 14 using a rolling shutter method and outputs to the light source apparatus 3, timing information which allows distinguishing between an all line exposure period which is a period during which pixels located on all horizontal lines of the image pickup device 14 are exposed at the same time, and a non-all line exposure period which is a period other than the all line exposure period. Then, in accordance with such operation of the video processor 4, for example, as illustrated in FIG. 3, image pickup operation which sequentially performs exposure at exposure timings different for each horizontal line of the image pickup device 14 is performed for each one field period TF2, and timing information TJ2 indicating the all line exposure period TAL and the non-all line exposure period TNL is outputted to the light source apparatus 3.

Further, the video processor 4 outputs the light amount control parameter information PJ2 read from the memory 15 in accordance with connection of the electrical connector 10 to the light source apparatus 3.

The control unit 29 sets a light amount control pattern GP2 for adjusting the light amount of the G light by changing a current value of a drive signal for driving the green LED 22 between a maximum current value I3 and a minimum current value I4 based on the light amount control parameter information PJ2 and the timing information TJ2 outputted from the video processor 4 and further changing a pulse width of the drive signal based on a maximum pulse width PW3 in the all line exposure period TAL, a minimum pulse width PW4 in the all line exposure period TAL and a pulse width PWC in the non-all line exposure period TNL.

That is, when the type of the image pickup device 14 is a CMOS, the light amount control parameter information PJ2 including information indicating the maximum current value I3 and the minimum current value I4 and information indicating the maximum pulse width PW3 and the minimum pulse width PW4 is stored in advance in the memory 15. Further, when the type of the image pickup device 14 is a CMOS, the maximum pulse width PW3 corresponds to a maximum light emitting period in the all line exposure period TAL, and the minimum pulse width PW4 corresponds to a minimum light emitting period in the all line exposure period TAL.

Note that, it is assumed that, for example, the maximum pulse width PW3 is set as a pulse width matching the all line exposure period TAL in the one field period TF2. Further, it is assumed that, for example, the pulse width PWC is set as a pulse width matching the non-all line exposure period TNL in the one field period TF2.

Here, for example, as illustrated in FIG. 3, the light amount control pattern GP2 is set as a control pattern such that, when the light amount of the G light is reduced, in the drive signal supplied from the LED driving unit 28 to the green LED 22, control for reducing the current value from 13 to 14, control for reducing the pulse width of the all line exposure period TAL from PW3 to PW4, control for setting the current value of the non-all line exposure period TNL at 0 while setting the pulse width of the all line exposure period TAL at PW5 corresponding to PW4+PWC, and control for reducing the pulse width of the all line exposure period TAL from PW5 to PW4 are performed in this order for each one field period TF2. Further, the light amount control pattern GP2 is set as a control pattern such that, for example, when the light amount of the G light is increased, in the drive signal supplied from the LED driving unit 28 to the green LED 22, control for increasing the pulse width of the all line exposure period TAL from PW4 to PW5, control for setting the pulse width of the non-all line exposure period TNL at PWC while setting the pulse width of the all line exposure period TAL at PW4, control for increasing the pulse width of the all line exposure period TAL from PW4 to PW3, and control for increasing the current value from 14 to 13 are performed in this order for each one field period TF2. Note that, in the light amount control pattern GP2, when the pulse width is reduced from PW3 to PW4 and when the pulse width is reduced from PW5 to PW4, control is performed so that a quenching period of the green LED 22 is set in the order closer to a start timing of the all line exposure period TAL.

That is, when the image pickup device 14 performs image pickup operation using the rolling shutter method, the control unit 29 sets the light amount control pattern GP2 which changes at least one of a light emission period (corresponding to the pulse width) and emission intensity (corresponding to the current value) in the all line exposure period TAL.

On the other hand, the control unit 29 having a function as an exposure period setting unit sets an exposure period ET2 of the optical sensor 22b so as to include an end timing tb of the all line exposure period TAL (one field period TF2) and to be less than the minimum pulse width PW4 based on the timing information TJ2 outputted from the video processor 4 and the light amount control pattern GP2 (see FIG. 3).

Note that, according to the present embodiment, for example, the exposure period ET2 of the optical sensor 22b may be set so as to include a start timing of the all line exposure period TAL and to be less than the minimum pulse width PW4.

That is, according to the operation, or the like, as described above, the exposure period ET2 is set so as to be able to favorably detect the light amount of the G light during a lighting period of the green LED 22 according to the light amount control pattern GP2.

Figure 4:
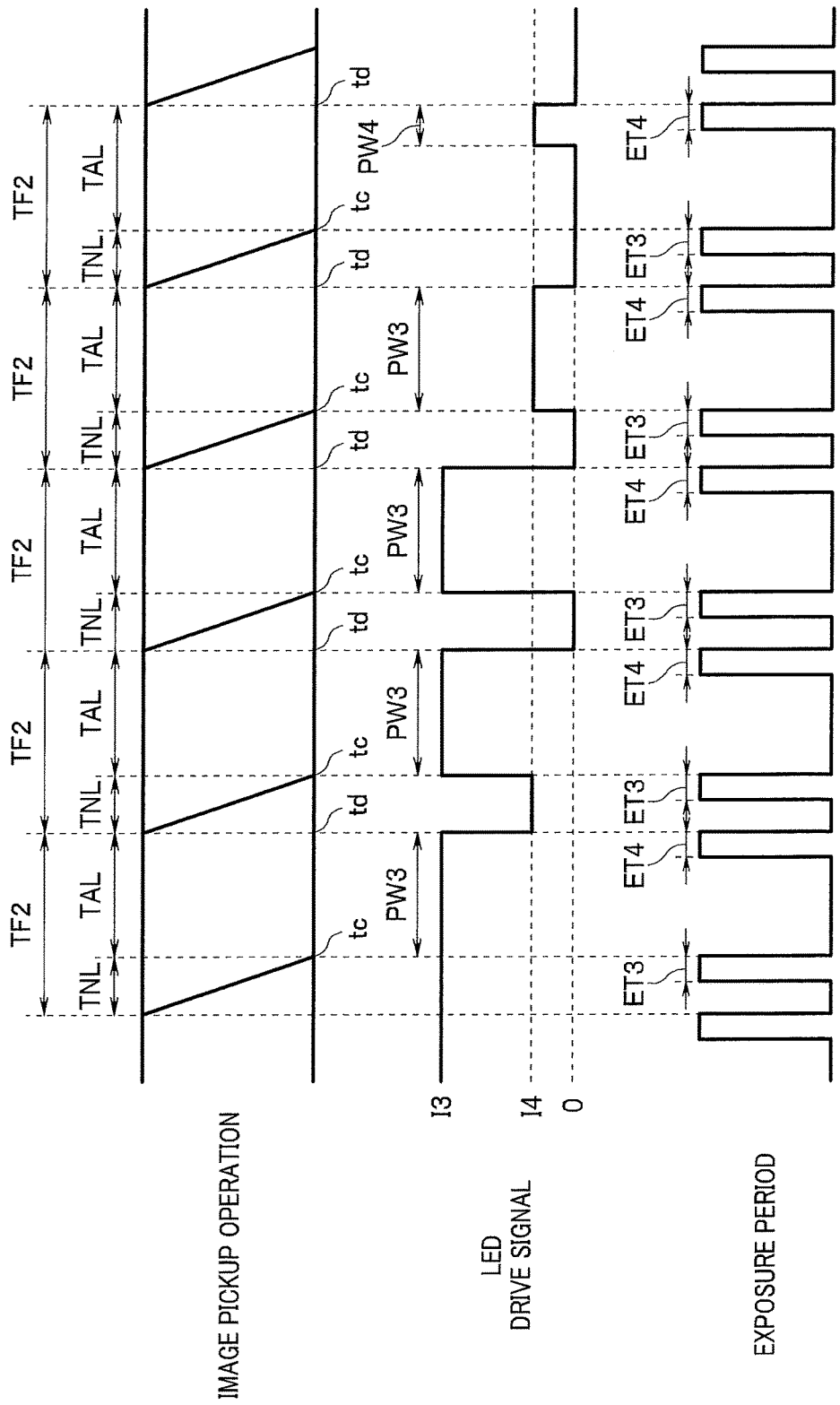
FIG. 4 is a timing chart for explaining an example, which is different from the examples in FIG. 2 and FIG. 3, of the operation of the image pickup system according to the embodiment.

Note that, when the type of the image pickup device 14 is a CMOS, the exposure period of the optical sensor 22b may be set using a setting method which will be described below. FIG. 4 is a timing chart explaining an example different from the examples in FIG. 2 and FIG. 3, of the operation of the image pickup system according to the embodiment.

When, for example, it is detected that the type of the image pickup device 14 is a CMOS based on the image pickup device information read from the memory 15 in accordance with connection of the electrical connector 10, the video processor 4 performs control for operating the image pickup device 14 using the rolling shutter method and outputs to the light source apparatus 3, timing information which allows distinguishing between an all line exposure period which is a period during which pixels located on all horizontal lines of the image pickup device 14 are exposed at the same time and a non-all line exposure period which is a period other than the all line exposure period. Then, in accordance with such operation of the video processor 4, for example, as illustrated in FIG. 4, image pickup operation which sequentially performs exposure at exposure timings different for each horizontal line of the image pickup device 14 is performed during one field period TF2, and the timing information TJ2 indicating the all line exposure period TAL and the non-all line exposure period TNL is outputted to the light source apparatus 3.

Further, the video processor 4 outputs the light amount control parameter information PJ2 read from the memory 15 in accordance with connection of the electrical connector 10 to the light source apparatus 3.

The control unit 29 sets a light amount control pattern GP3 for adjusting the light amount of the G light by changing a current value of a drive signal for driving the green LED 22 between a maximum current value l3 and a minimum current value l4 based on the light amount control parameter information PJ2 and the timing information TJ2 outputted from the video processor 4, and further changing a pulse width of the drive signal based on a maximum pulse width PW3 in the all line exposure period TAL and a minimum pulse width PW4 in the all line exposure period TAL.

Here, for example, as illustrated in FIG. 4, the light amount control pattern GP3 is set as a control pattern such that, when the light amount of the G light is reduced, in the drive signal supplied from the LED driving unit 28 to the green LED 22, control for reducing the current value of the non-all line exposure period TNL from 13 to 14, control for reducing the current value of the non-all line exposure period from 14 to 0, control for reducing the current value of the all line exposure period TAL from 13 to 14, and control for reducing the pulse width of the all line exposure period TAL from PW3 to PW4 are performed in this order for each one field period TF2. Further, the light amount control pattern GP3 is set as a control pattern such that, for example, when the light amount of the G light is increased, in the drive signal supplied from the LED driving unit 28 to the green LED 22, control for increasing the pulse width of the all line exposure period TAL from PW4 to PW3, control for increasing the current value of the all line exposure period TAL from 14 to 13, control for increasing the current value of the non-all line exposure period TNL from 0 to 14, and control for increasing the current value of the non-all line exposure period TNL from 14 to 13 are performed in this order for each one field period TF2. Note that, it is assumed that, in the light amount control pattern GP3, when the pulse width is reduced from PW3 to PW4, control is performed so that a quenching period of the green LED 22 is set in the order closer to a start timing of the all line exposure period TAL.

That is, when the image pickup device 14 performs image pickup operation using the rolling shutter method, the control unit 29 sets the light amount control pattern GP3 which changes at least one of a light emitting period (corresponding to the pulse width) and emission intensity (corresponding to the current value) in the all line exposure period TAL, and emission intensity (corresponding to the current value) in the non-all line exposure period TNL.

On the other hand, the control unit 29 having a function as an exposure period setting unit, sets an exposure period ET3 of the optical sensor 22b so as to include an end timing tc of the non-all line exposure period TNL and to be less than the minimum pulse width PW4 based on the timing information TJ2 outputted from the video processor 4 and the light amount control pattern GP3, and further sets an exposure period ET4 of the optical sensor 22b so as to include an end timing td of the all line exposure period TAL (one field period TF2) and to be less than the minimum pulse width PW4 (see FIG. 4).

Note that, according to the present embodiment, for example, the exposure period ET3 of the optical sensor 22b may be set so as to include a start timing of the non-all line exposure period TNL and to be less than the minimum pulse width PW4. Further, according to the present embodiment, for example, the exposure period ET4 of the optical sensor 22b may be set so as to include a start timing of the all line exposure period TAL and to be less than the minimum pulse width PW4.

That is, according to the operation, or the like, as described above, the exposure period ET4 is set so as to be able to favorably detect the light amount of the G light during the lighting period of the green LED 22 according to the light amount control pattern GP3. Further, according to the operation, or the like, as described above, for example, even when control is performed based on a light amount control pattern such as the light amount control pattern GP3 in which the current value of the all line exposure period TAL is different from the current value of the non-all line exposure period TNL within the one field period TF2, it is possible to favorably detect the light amount of the G light.

Note that, according to the present embodiment, for example, the exposure period ET5 of the optical sensor 22b may be set so as to interpose a start timing or an end timing of the all line exposure period TAL in the exposure period ET5, and the light amount of the G light may be detected based on a ratio between the exposure period ET6 included in the all line exposure period TAL among the exposure period ET5 and the exposure period ET7 included in the non-all line exposure period TNL among the exposure period ET5. Further, according to the present embodiment, for example, the above-described exposure periods ET6 and ET7 may be respectively set so as to be less than the minimum pulse width PW4.

Further, according to the present embodiment, for example, two or more exposure periods including the exposure period ET3 may be set within the non-all line exposure period TNL. Further, according to the present embodiment, for example, two or more exposure periods including the exposure period ET4 may be set within the all line exposure period TAL.

As described above, according to the present embodiment, it is possible to perform control for driving each LED using the light amount control pattern according to the image pickup operation of the image pickup device 14 and favorably detect the light amount of the light emitted from each LED according to the light amount control pattern at the optical sensors 21b to 23b. Therefore, according to the present embodiment, it is possible to appropriately adjust color balance of illumination light while taking into account the type of the image pickup device.

Note that the present invention is not limited to the above-described each embodiment, and various modification and application are, of course, possible without deviating from the intent of the invention.

What is claimed is:

1. An image pickup system which picks up an optical image of an object illuminated with light of a plurality of colors emitted from a plurality of semiconductor light emitting elements with an image pickup device, the image pickup system comprising:
    a light source apparatus comprising the plurality of semiconductor light emitting elements, an optical sensor configured to detect each of light amounts of the light of the plurality of colors emitted from the plurality of semiconductor light emitting elements, and a controller including hardware;
    an endoscope comprising the image pickup device, wherein the endoscope is configured to be detachably connected to the light source apparatus; and
    a drive circuit configured to drive the plurality of semiconductor light emitting elements,
    wherein the image pickup device provided at the endoscope is configured to perform image pickup operation using either a global shutter method or a rolling shutter method, and
    wherein the controller is configured to:
        detect whether the image pickup device performs image pickup operation using the global shutter method or the rolling shutter method;
        generate brightness control information for setting brightness of an image picked up by the image pickup device as target brightness;
        adjust color balance of the light of the plurality of colors based on the light amounts of the plurality of colors detected at the optical sensor;
        control driving of the plurality of light emitting elements by the drive circuit so that light emission amounts of the light of the plurality of colors are adjusted based on the brightness control information and a light amount control pattern; and
        when it is detected that the image pickup device provided at the endoscope connected to the light source apparatus performs image pickup operation using the rolling shutter method, set a control pattern which changes at least one of a light emitting period and emission intensity in an all line exposure period during which pixels located on all horizontal lines of the image pickup device are exposed at a same time and emission intensity in a non-all line exposure period other than the all line exposure period as the light amount control pattern, and set a first exposure timing of the optical sensor so as to include a start timing or an end timing of the all line exposure period and set a second exposure timing of the optical sensor so as to include a start timing or an end timing of the non-all line exposure period.

2. The image pickup system according to claim 1, wherein, when it is detected that the image pickup device provided at the endoscope connected to the light source apparatus performs image pickup operation using the global shutter method, the controller is configured to set a control pattern which changes at least one of a light emitting period and emission intensity in an all pixel exposure period during which all pixels of the image pickup device are exposed at a same time as the light amount control pattern, and set an exposure timing of the optical sensor so as to include a start timing or an end timing of the all pixel exposure period.

3. The image pickup system according to claim 1, wherein the controller is configured to set an exposure period of the optical sensor including the exposure timing of the optical sensor.

4. The image pickup system according to claim 3, wherein the controller is configured to set the exposure period of the optical sensor so as to be less than a minimum light emitting period of the plurality of semiconductor light emitting elements.

5. An image pickup system which picks up an optical image of an object illuminated with light of a plurality of colors emitted from a plurality of semiconductor light emitting elements with an image pickup device, the image pickup system comprising:
 a light source apparatus comprising the plurality of semiconductor light emitting elements, an optical sensor configured to detect each of light amounts of the light of the plurality of colors emitted from the plurality of semiconductor light emitting elements, and a controller including hardware;
 an endoscope comprising the image pickup device, wherein the endoscope is configured to be detachably connected to the light source apparatus; and
 a drive circuit configured to drive the plurality of semiconductor light emitting elements,
 wherein the image pickup device provided at the endoscope is configured to perform image pickup operation using either a global shutter method or a roller shutter method, and
 wherein the controller is configured to:
  detect whether the image pickup device performs image pickup operation using the global shutter method or the rolling shutter method;
  generate brightness control information for setting brightness of an image picked up by the image pickup device as target brightness;
  adjust color balance of the light of the plurality of colors based on the light amounts of the plurality of colors detected at the optical sensor;
  control driving of the plurality of light emitting elements by the drive circuit so that light emission amounts of the light of the plurality of colors are adjusted based on the brightness control information and a light amount control pattern; and
  when it is detected that the image pickup device provided at the endoscope connected to the light source apparatus performs image pickup operation using the rolling shutter method, set a control pattern which changes at least one of a light emitting period and emission intensity in an all line exposure period during which pixels located on all horizontal lines of the image pickup device are exposed at a same time and emission intensity in a non-all line exposure period other than the all line exposure period as the light amount control pattern, and set an exposure timing of the optical sensor so as to interpose a start timing or an end timing of the all line exposure period in the exposure timing.

6. The image pickup system according to claim 5, wherein, when it is detected that the image pickup device provided at the endoscope connected to the light source apparatus performs image pickup operation using the global shutter method, the controller is configured to set a control pattern which changes at least one of a light emitting period and emission intensity in an all pixel exposure period during which all pixels of the image pickup device are exposed at a same time as the light amount control pattern, and set an exposure timing of the optical sensor so as to include a start timing or an end timing of the all pixel exposure period.

7. The image pickup system according to claim 5, wherein the controller is configured to set an exposure period of the optical sensor including the exposure timing of the optical sensor.

8. The image pickup system according to claim 7, wherein the controller is configured to set the exposure period of the optical sensor so as to be less than a minimum light emitting period of the plurality of semiconductor light emitting elements.

9. An image pickup system which picks up an optical image of an object illuminated with light of a plurality of colors emitted from a plurality of semiconductor light emitting elements with an image pickup device, the image pickup system comprising:
 a light source apparatus comprising the plurality of semiconductor light emitting elements, an optical sensor configured to detect each of light amounts of the light of the plurality of colors emitted from the plurality of semiconductor light emitting elements, and a controller including hardware;
 an endoscope comprising the image pickup device, wherein the endoscope is configured to be detachably connected to the light source apparatus; and
 a drive circuit configured to drive the plurality of semiconductor light emitting elements,
 wherein the image pickup device provided at the endoscope is configured to perform image pickup operation using either a global shutter method or a roller shutter method, and
 wherein the controller is configured to:
  detect whether the image pickup device performs image pickup operation using the global shutter method or the rolling shutter method;
  generate brightness control information for setting brightness of an image picked up by the image pickup device as target brightness;
  control driving of the plurality of light emitting elements by the drive circuit so that light emission amounts of the light of the plurality of colors are adjusted based on the brightness control information and a light amount control pattern;
  set an exposure timing of the optical sensor according to image pickup operation of the image pickup device; and
  set the light amount control pattern and further adjust color balance of the light of the plurality of colors by controlling the drive circuit to drive a reference semiconductor light emitting element which emits the light of the predetermined color, included in the plurality of semiconductor light emitting elements, based on the set light amount control pattern, and controlling the drive circuit to drive each of the semiconductor light emitting elements other than the reference semiconductor light emitting element included in the plurality of semiconductor light emitting elements, based on the light amounts of the light of the plurality of colors detected during the exposure period of the optical sensor and the light amount control pattern.

10. The image pickup system according to claim 9, wherein the controller is configured to set an exposure period of the optical sensor including the exposure timing of the optical sensor.

11. The image pickup system according to claim 10, wherein the controller is configured to set the exposure period of the optical sensor so as to be less than a minimum light emitting period of the plurality of semiconductor light emitting elements.

* * * * *